(12) United States Patent
Cheung

(10) Patent No.: US 6,927,059 B2
(45) Date of Patent: Aug. 9, 2005

(54) COMPOSITIONS AND METHODS FOR IDENTIFYING AGENTS WHICH REGULATE AUTOLYTIC PROCESSES IN BACTERIA

(75) Inventor: Ambrose Cheung, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 272 days.

(21) Appl. No.: 10/290,143

(22) Filed: Nov. 6, 2002

(65) Prior Publication Data

US 2003/0124597 A1 Jul. 3, 2003

Related U.S. Application Data

(63) Continuation-in-part of application No. 10/092,264, filed on Mar. 6, 2002.
(60) Provisional application No. 60/273,791, filed on Mar. 6, 2001, provisional application No. 60/312,546, filed on Aug. 15, 2001, and provisional application No. 60/329,140, filed on Oct. 12, 2001.

(51) Int. Cl.[7] .............................................. C12N 15/63
(52) U.S. Cl. ............................... 435/320.1; 435/252.7; 536/24.1
(58) Field of Search ........................... 435/320.1, 252.7; 536/24.1

(56) References Cited

PUBLICATIONS

Brunskill, E.W., et al. (1996) J. Bacteriol. 178(3), 611–618.*
Brunskill et al., "Identification of LytSR–Regulated Genes from *Staphylococcus aureus*", Journal of Bacteriology 1996 5810–5812.
Cole et al., "The EBV–Hybridoma Technique and Its Application to Human Lung Cancer", Monoclonal Antibodies and Cancer Therapy 1985 77–96.
Fournier et al., "A New Two–Component Regulatory System Involved in Adhesion, Autolysis, and Extracellular Proteolytic Activity of *Staphylococcus aureus*", Journal of Bacteriology 2000 182(14):3955–3964.
Fujimoto et al., "Analysis of Genetic Elements Controlling *Staphylococcus aureus* lrgAB Expression:Potential Role of DNA Topology in Star A Regulation", Journal of Bacteriology 2000 182(17):4822–4828.
Ochiai T., "*Staphylococcus aureus* Produces Autolysin–Susceptible Cell Walls during Growth in a High–NaCI and Low–Ca2+ Concentration Medium", Microbiol. Immunol. 2000 44(2):97–104.
Köhler et al., "Continuous cultures of fused cells secreting antibody of predefined specificity", Nature 1975 256:495–497.
Kozbor et al., "The production of monoclonal antibodies from human lymphocytes", Immunology Today 1983 4(3):72–79.
Pinho et al., "Cloning, Characterization, and Inactivation of the Gene pbpC, Encoding Penicillin–Binding Protein 3 of *Staphylococcus aureus*", Journal of Bacteriology 2000 182(4):1074–1079.
Ramadurai et al., "Molecular Cloning, Sequencing, and Expression of lytM, a Unique Autolytic Gene of *Staphylococcus aureus*", Journal of Bacteriology 1997/ 79(11):3625–3631.
Cheung et al., "Insertional Inactivation of a Chromosomal Locus That Modulates Expression of Potential Virulence Determinants in *Staphylococcus aureus*", J. Bateriology 1995 177(11):3220–3226.

* cited by examiner

*Primary Examiner*—Charles L. Patterson, Jr.
(74) *Attorney, Agent, or Firm*—Licata & Tyrrell P.C.

(57) ABSTRACT

A nucleic acid sequence which regulates the autolytic activity of bacteria is provided. Methods for identifying and using agents which interact with the gene to inhibit bacterial growth and infectivity also are provided.

6 Claims, 4 Drawing Sheets

```
Sa-Rat    1  ms-------- -------DQH NLKEQLCFSL YNAQRQVNRY (SEQ ID NO:3)
Ba-MarR   1  m--------- -----TEDSL HLDNQLCFSI YACSREVTRF (SEQ ID NO:4)
Ca-MarR   1  mqdg------ -------EQL KLKYQLCFSI YASSRAITKV (SEQ ID NO:5)
Xa-MarR   1  mpspqvscqT P----THDPL LLENQVCFPL YSASNAVIRA (SEQ ID NO:6)
Xc-OhrR   1  mdta-----T PttdrTNALL QLDNQLCFAL YSANLAMHKL (SEQ ID NO:7)
Sa-SarA   1  maitkind-- ---------- ------CFEL LSMVTYADKL (SEQ ID NO:8)
             *  *       *****  ********** **********
                                ********** **********
                                   ******  **********
                                   ****** **********

Sa-Rat    36 YsnkVFKKYN LTYPQFLVLT ILWDESPVN- -VKKVVTELA (SEQ ID NO:3)
Ba-MarR   36 YRP-YLEEMG ITYPQYITLL VLWEQDGLT- -VKEIGERLF (SEQ ID NO:4)
Ca-MarR   37 YKP-FLNKLG LTYPQYLVML VLWEEKSIT- -LKDLGNKLY (SEQ ID NO:5)
Xa-MarR   46 YRP-LLEQLD ITYSQYLVLL VLWQQNGIN- -VKDLGIKLH (SEQ ID NO:6)
Xc-OhrR   45 YRG-LLKTLD LTYPQYLVML VLWENDGRS- -VSEIGERLY (SEQ ID NO:7)
Sa-SarA   32 KSL-IKKEFS ISFEEFAVLT YISENKEkey yLKDIINHLN (SEQ ID NO:8)
             ***  ****** ********** ********* **********
             ***  ****** ********** ********* *********
             ***  ****** ********** ********* *********
             ***  ****** ********** *****  ** *********
                        ********** ****   *   ****  **

Sa-Rat    84 LDTGTVSPLL KRMEQVDLIK RERSEVDQRE VFIHLTDKSE (SEQ ID NO:3)
Ba-MarR   84 LDSGTLTPML KRMESLNLVK RVRSKEDERK VCIELTEQGK (SEQ ID NO:4)
Ca-MarR   85 LDSGTLTPLL KRLEGLNLIV RKRSSLDERL LSVNITEKGE (SEQ ID NO:5)
Xa-MarR   94 LDSGTLTPLL KRLEAKGIVE RRRSSSDERV RELFLTPAGF (SEQ ID NO:6)
Xc-OhrR   93 LDSATLTPLL KRLESAGLLT RTRAAHDERQ VIIGLADAGR (SEQ ID NO:7)
Sa-SarA   82 YKQPQVVKAV KILSQEDYFD KKRNEHDERT VLI1------ (SEQ ID NO:8)
             ********** ********** ********** **********
             ********** ********** ********** **********
             ********** ********** *********   *
             ********** ********** *********
             ********** ********** *********

Sa-Rat   134 TIRPELSNAS DKVASASSLS QDEVKELNRL LGKVIHAFDE (SEQ ID NO:3)
Ba-MarR  134 DLQDKACSLP TTMATNLGIT EQEYRSLLIQ LNKLIETMKt (SEQ ID NO:4)
Ca-MarR  135 ELKKDALEIP SCVLKSTNTD IETLKRIKTD IDLLLKNLS- (SEQ ID NO:5)
Xa-MarR  144 ALQEQARSVP NEMLCKFDLS LEELISLKTL CEKILHTLD- (SEQ ID NO:6)
Xc-OhrR  143 ALRSKAGAVP EQVFCASACS LEELRQLKQE LEKLRTSLGa (SEQ ID NO:7)
Sa-SarA  111 ---------- -----VNAQQ RKKIESLLSR VNKRITEANN (SEQ ID NO:8)
             ********** ********** ********** **********
             **********

Sa-Rat   134 TKEk--- (SEQ ID NO:3)
Ba-MarR  134 indrkge (SEQ ID NO:4)
Ca-MarR  135 ------- (SEQ ID NO:5)
Xa-MarR  144 ------- (SEQ ID NO:6)
Xc-OhrR  143 a------ (SEQ ID NO:7)
Sa-SarA  111 EIEl--- (SEQ ID NO:8)
             ***
```

FIG. 4

COMPOSITIONS AND METHODS FOR IDENTIFYING AGENTS WHICH REGULATE AUTOLYTIC PROCESSES IN BACTERIA

This application is a continuation-in-part of U.S. patent application Ser. No. 10/092,264, filed Mar. 6, 2002 which is incorporated herein by reference and which claims benefit under 35 U.S.C. §119 of U.S. provisional applications Ser. No. 60/273,791, filed on Mar. 6, 2001; 60/312,546, filed on Aug. 15, 2001; and Ser. No. 60/329,140, filed on Oct. 12, 2001, whose contents are incorporated herein by reference in their entireties.

This invention was made in the course of research sponsored by the National Institutes of Health (NIH Grant No. RO1-AI37142). The U.S. government may have certain rights in this invention.

BACKGROUND

*Staphylococci* are hardy and ubiquitous colonizers of human skin and mucous membranes and were among the first human pathogens identified. These bacteria constitute a medically important genera of microbes as they are known to produce two types of disease, invasive and toxigenic.

Invasive infections are characterized generally by abscess formation affecting both skin surfaces and deep tissues. In addition, *Staphylococcus aureus* (*S. aureus*) is the second leading cause of bacteremia in cancer patients. Osteomyelitis, septic arthritis, septic thrombophlebitis and acute bacterial endocarditis are also relatively common.

There are also at least three clinical conditions resulting from the toxigenic properties of *Staphylococci*. The manifestation of these diseases result from the actions of exotoxins as opposed to tissue invasion and bacteremia. These conditions include: *Staphylococcal* food poisoning, scalded skin syndrome and toxic shock syndrome.

*S. aureus* are non-motile, non-sporulating gram-positive cocci 0.5–1.5 μm in diameter, that occur singly and in pairs, short chains, and irregular three-dimensional clusters. *S. aureus* can grow over a wide range of environmental conditions, but they grow best at temperatures between 30° C. and 37° C. and at a neutral pH. They are resistant to desiccation and to chemical disinfection, and they tolerate NaCl concentrations up to 12%. However, growth of *S. aureus* becomes unusually sensitive to a high-NaCl concentration by decreasing the $Ca^{2+}$ concentration in growth media allowing for autolysis (Ishikawa, *Microbiology and Immunology*, 2000: 44(2):97–104).

Humans constitute the major reservoir of the *S. aureus* bacteria. The cross-sectional carriage rate in adults is 15 to 40 percent. The mucous membranes of the anterior nasopharynx are the principal site of carriage. Other sites include the axillae, the vagina, the perineum and occasionally the gastrointestinal tract. Colonization by *S. aureus* may be intermittent or persistent and is probably influenced by both microbial and host factors as well as by the nature of the competing non-*Staphylococcal* flora.

The frequency of *S. aureus* infections has risen dramatically in the past 20 years. This has been attributed to two main factors. The first factor is an increasing population of people with weakened immune systems. The second factor has been the emergence of multiple antibiotic resistant strains. It is no longer uncommon to isolate *S. aureus* strains which are resistant to some or all of the standard antibiotics. Active efflux of various toxic compounds from the cell to the outer medium is a universal mechanism that bacteria have evolved to protect themselves against the adverse effects of their environments. Antibiotics are expelled from the cells by membrane transporter proteins called multidrug resistance (MDRs) pumps. The NorA protein of *S. aureus* is an MDR pump that mediates the active efflux of hydrophilic fluoroquinolones from the cell (Ubukata, et al. *Antimicrob. Agents Chemother.*, 1989: 33(9):1535–9), conferring low-level resistance upon the organism. NorA is also capable of transporting additional structurally diverse compounds, indicating that it has a broad substrate specificity. NorR, a protein that shares 60% similarity with *B. subtilis* MarR and *S. aureus* SarA regulatory proteins, may function to repress the transcription of NorA (Truong-Bolduc, et al., *ASM 2001 General Meeting*, May 22, 2001: Abstract A-56).

The rise in the frequency of *S. aureus* infections has created a demand for both new anti-microbial agents and diagnostic tests for this organism. Accordingly, there is a need for better understanding of factors which regulate infectivity and growth of *S. aureus*. Genes identified as involved in the infectivity and/or growth of *S. aureus* include the arlS regulator, involved in adhesion (Fournier and Hooper, *Journal of Bacteriology*, 2000: 182(14): 3955–64), the pbpC gene, which affects the rate of autolysis (Pinho et al., *Journal of Bacteriology*, 2000: 182(4): 1074–9), the atl gene, which encodes a protein having amidase and N-acetylglucosaminidase activity (Sugai, et al., *Journal of Bacteriology*, 1997:179:2958–2962), lytN (Sugai, *Journal of Infection and Chemotherapy*, 1997:3:113–127), lytRS (Brunskill and Bayles, *Journal of Bacteriology*, 1996: 178(19):5810–2), lrgA and lrgB (Fujimoto et al., *Journal of Bacteriology*, 2000: 182(17): 4822–8), and lytM identified in autolysis-deficient mutants of *S. aureus* (Ramadurai and Jayaswal, *Journal of Bacteriology*, 1997: 179(11):3625–31).

A new polypeptide of *S. aureus* which regulates autolytic processes has now been identified. The nucleic acid sequences encoding this polypeptide, referred to herein as Rat, regulator of autolytic activity, which regulates autolytic processes has been cloned and sequenced. Further, it has been shown that mutations in the nucleic acid sequences encoding Rat render *S. aureus* more susceptible to lysis by antibiotics.

SUMMARY OF THE INVENTION

The present invention provides a method of identifying agents that modulate autolytic activity of *S. aureus* and other bacteria through interaction with the nucleic acid sequence (SEQ ID NO:1) encoding Rat. These agents are expected to be useful in the inhibition of growth of *S. aureus* and other bacteria and in the treatment of hosts infected by *S. aureus* and other bacteria. These agents may be used alone or in combination with an antibiotic such as penicillin to promote lysis of the bacteria.

Accordingly, another object of the present invention is to provide methods for modulating autolytic activity of *S. aureus* and other bacteria to inhibit their growth and infectivity by contacting the bacteria with an agent which interacts with the nucleic acid sequence SEQ ID NO:1) encoding Rat or a fragment thereof.

Yet another object of the present invention is to provide anti-bacterial agents which comprise a compound which prevents or inhibits infections by *S. aureus* or other bacteria via interaction with the nucleic acid sequence encoding SEQ ID NO:1) Rat or a fragment thereof.

BRIEF DESCRIPTION OF THE DRAWINGS

FIG. 4 shows a multiple sequence alignment of Rat with other bacterial transcriptional regulators generated by DIALIGN 2 (Morgenstern, *Bioinformatics*, 1999: 15:211–218). *Staphylococcus aureus* Rat (Sa-Rat; SEQ ID NO:3); *Bacillus anthracis* MarR (Ba-MarR; SEQ ID NO:4), accession number NP_658498; *Clostridium acetobutylicum* MarR (Ca-MarR; SEQ ID NO:5), accession number NP_350250; *Xanthomonas axonopodis* MarR (Xa-MarR; SEQ SEQ ID NO:6), accession number NP_641789; *Xanthomonas campestris* OhrR (Xc-OhrR; SEQ ID NO:7), accession number AAK62673; and *Staphylococcus aureus* SarA (Sa-SarA; SEQ ID NO:8), accession number BAB94445. Capital letters denote the majority. The number of "*" characters below the alignment reflects the degree of conserved residues among sequences.

DETAILED DESCRIPTION OF THE INVENTION

Figure 1:
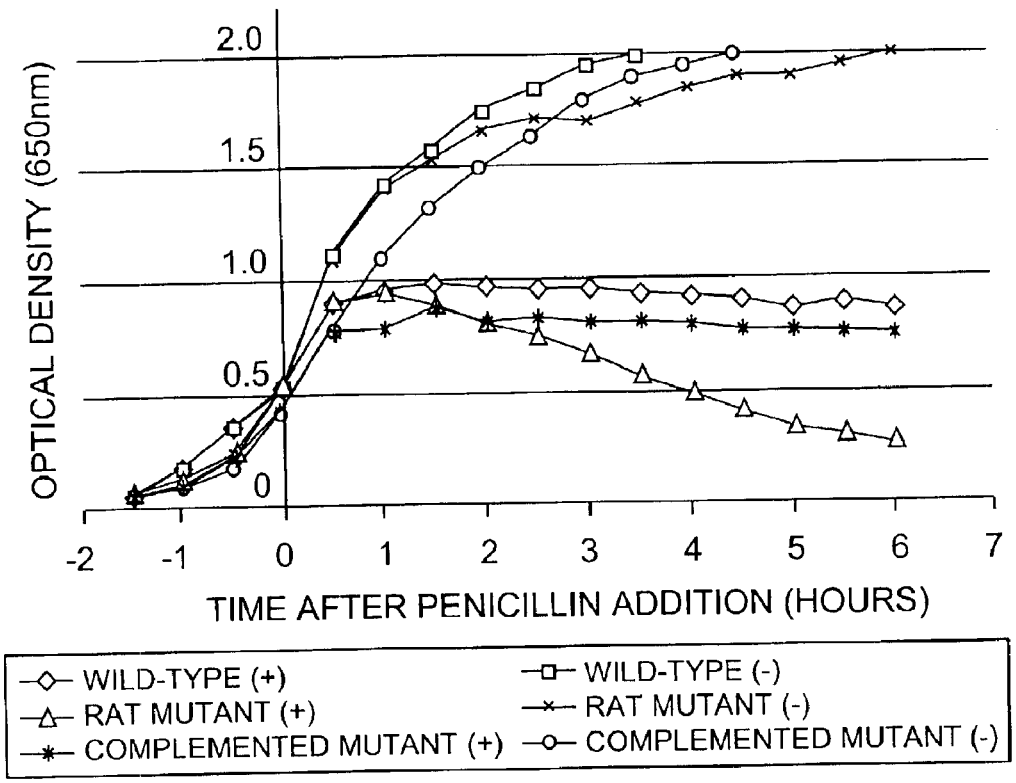
FIG. 1 graphically demonstrates the effect that subinhibitory concentrations of penicillin have on the rat mutant as compared to wild-type.

*S. aureus* is the most prevalent human pathogen in the Staphylococcal genus. It remains a major public health concern due to its tenacity, potential destructiveness and increasing resistance to antimicrobial agents. Much research has been focused on identifying genes or gene products of *S. aureus* which serve as targets in the development of new antibacterial agents.

Using transposon mutagenesis, a nucleic acid (SEQ ID NO:1) encoding Rat (regulator of autolytic activity), which regulates expression of polypeptides involved in autolytic processes of *S. aureus*, has been identified. The phrase, "which regulates expression of polypeptides involved in autolytic processes" used herein means that the nucleic acid sequence or polypeptide encoded thereby controls, modulates or regulates the expression of polypeptides involved in autolytic processes such as autolytic enzymes (e.g., murein hydrolase, cell wall hydrolase, glycylglycine endopeptidase), polypeptides involved in environmental signaling, antibiotic efflux, the secretion of autolysins or other autolytic processes. A Tn551 transposon library of *S. aureus* strain RN6390 was constructed. The library was screened for genes that affected expression of genes encoding the capsular polysaccharide (cap genes—16 genes encoded within the cap operon) of *S. aureus*. Using the cap promoter linked to the GFP reporter gene (green fluorescent protein), a mutant (ALC2011) was identified that displayed significantly lower cap promoter activity. However, upon growing this mutant, it was discovered that this strain grew poorly in 03GL medium, reaching a maximum optical density of 0.8 when the parental strain could achieve an OD650 nm of 1.3 or higher. The defect was linked to the transposon insertion as this phenotype could be back-crossed into the parental strain yielding strain ACL2529. The region of the mutant chromosome where the transposon was inserted was subsequently sequenced; the sequence of the mutant locus is SEQ SEQ ID NO:2. This gene was designated rat, or regulator of autolytic activity. The rat mutant gene encodes a truncated protein of 134 residues in length. The rat mutant is a transposon mutant in which a Tn551 transposon is inserted at the 3' end of the polynucleotide sequence, yielding a truncated protein or polypeptide missing the last 13 amino acid residues of the wild-type protein. It is believed that the rat mutant is a partial gene knockout. By "knock-out" it is meant that an alteration in the target gene sequence occurs which results in an alteration of normal function of the target gene product.

Zymogram analysis revealed that the rat mutant strain displays significantly enhanced autolytic activity as compared to the wild-type. This defect in autolytic activity was restored upon complementation of the mutant. The rat mutant was complemented with an integration vector containing the entire rat gene. The complemented strain (ALC2012) grew to a higher optical density (OD650 nm) than the rat mutant strain and had lower cell wall hydrolase activities than the rat mutant.

The native rat sequence SEQ ID NO:1 encodes a 17-kDa protein of 147 residues in length. Forty-seven of the 147 residues (32%) are charged and the pI of Rat is predicted to be 7.38.

Rat plays a role in regulating autolytic activity of *S. aureus*. More specifically, in the presence of penicillin, the rat mutant was shown to readily increase lysis as compared to wild-type *S. aureus*. Furthermore, inactivation of the rat locus renders the *S. aureus* bacteria sensitive to lysis upon growth beyond the mid-log phase. To evaluate whether the cell lysis of the rat mutant was additive to the effect of a subinhibitory concentration of penicillin, 200 ng/ml of penicillin was added to a growing culture of the rat mutant at an OD650 nm of 0.5, corresponding to the mid-log phase. Upon addition of penicillin, the rat mutant exhibited a further reduction in optical density as the growth cycle progressed (FIG. 1) in contrast to the wild-type strain that displayed no increase in optical density (i.e., no growth). This finding is consistent with the additive effect of penicillin upon the lytic propensity of the rat mutant late in the growth cycle. Similar results were obtained using gentamicin and cephalothin. Upon plating these cultures on agar plates without antibiotic selection, it was found that the rat mutant has 1–2 log more kill than the parental strain. In comparison to the parental strain, the rat mutant with subinhibitory concentrations of penicillin has a 3–4 log kill than the parental strain with antibiotics.

Zymographic analysis of cell-associated murein hydrolases was performed to analyze the autolytic activity of the rat mutant. Bacterial cells were centrifuged, washed, and resuspended in SDS-gel loading buffer, heated for 3 minutes at 100° C., recentrifuged, and the supernatant applied to a SDS-gel containing heat-killed *S. aureus* RN4220. Following electrophoresis, the gel was soaked in 0.1 percent TRITON® X-100 at 37° C. overnight to hydrolyze RN4220 cells that had been attacked by autolytic enzymes in the cell extracts. After incubation, the gel was stained with one percent methylene blue and destained in water. Clear bands, indicating zones of murein hydrolase activity, were found to be enhanced in the rat mutant as compared to the wild-type control. As a positive control, a sarA mutant was utilized. The sarA gene normally represses murein hydrolase activity.

Figure 2:
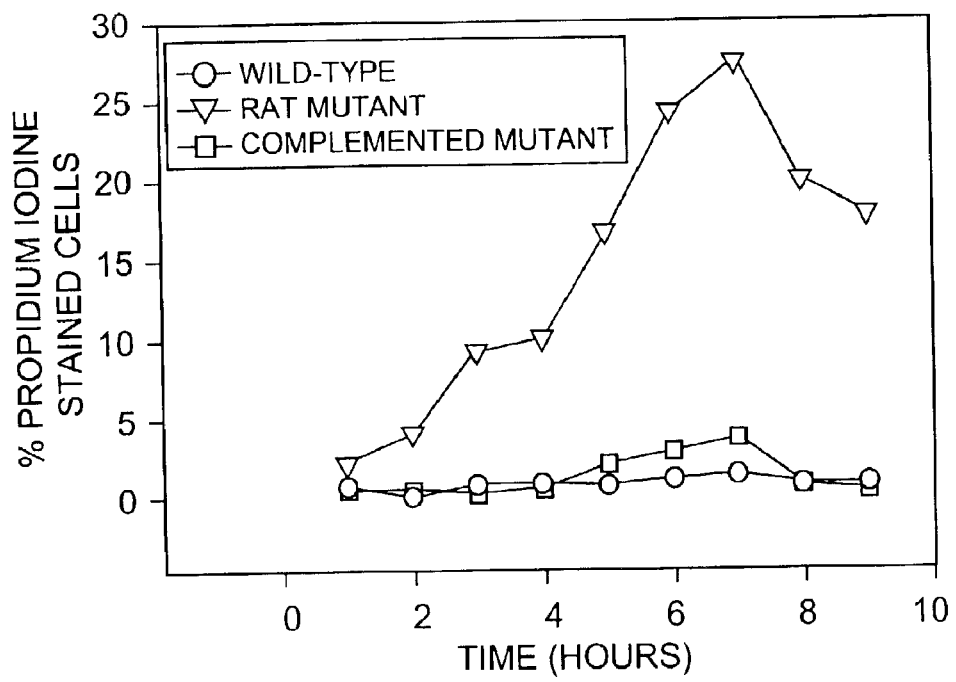
FIG. 2 graphically represents the viability of the rat mutant as compared to wild-type by propidium iodide staining.

The viability of rat mutant cells late in the growth cycle was determined by staining bacterial cells, obtained from different parts of the growth cycle, with propidium iodide. Penetration of the cell with propidium iodide indicates cell death or necrosis. Many of the rat mutant cells picked up the propidium iodide stain as the growth cycle lengthened (FIG. 2), thus accounting for the decrease in optical densities in the rat mutant during the late log phase.

The cell wall morphology of the rat mutant strain differs from the wild-type strain. rat mutant cells, undergoing division, exhibited a thicker cell wall than the wild-type strain. The outer contour of the rat mutant was rough while the surface of the wild-type cells was smooth. Irregularities in the outer cell wall, similar to that seen in the rat mutant, have previously been associated with altered autolytic activities in mutants. Bacterium possessing nucleotide sequences with a truncation of the rat gene or homolog thereof will also exhibit an increased sensitivity to lysis.

The bacterial cell wall is maintained by competing enzymes involved in the synthesis and lysis of the cell wall. Examples of autolytic enzymes include glucosamidase, muramidase, amidase, and endopeptidase. The synthesis of bacterial cell walls is a dynamic process requiring the precise regulation of both synthetic and autolytic activities. The autolytic activity of many bacteria is carefully controlled during the growth cycle in particular by regulatory elements. A disruption of these regulatory elements alters autolytic activity and leads to premature cell lysis during growth. The rat mutant has a defect in autolytic activity which prevents the mutant from reaching the stationary phase of growth. By northern blot analysis, it was shown that the rat mutation affects the expression of autolytic enyzmes such as LytN, LytM, and Atl. The cell wall hydrolase, lytN, and the glycylglycine endopeptidase, lytM, are up-regulated by the rat mutation. Conversely, the rat mutation down-regulated the regulators of autolytic activity, namely, LytS, LytR, LrgA, LrgB, ArlR, and ArlS. Furthermore, the rat mutation affects the expression of certain other S. aureus genes, e.g., hla, spa, abcA, scdA, and sspA. Both hla and scdA expression are down-regulated by the rat mutation, whereas both spa and abcA expression are up-regulated by the rat mutation.

A rat deletion mutant was also generated. Using a standard allelic replacement approach, the rat gene was replaced by an ermC cassette in a double-crossover event with the temperature-sensitive plasmid pCL52.2. With serial and frequent temperature shifts to the non-permissive temperature, a rat deletion mutant (ACL2530) was obtained and confirmed by Southern blot and PCR analyses. No detectable rat mRNA was observed by northern blot analysis in the rat deletion mutant. The rat deletion mutant was complemented with an integration vector containing the entire rat locus and rat expression in this strain (ACL2531) was restored to near normal levels.

Similar to the rat transposon mutant, the rat deletion mutant was unable to grow to an OD650 nm of 1.7 (early-stationary). Furthermore, in the presence of 100 μg penicillin (3×MIC), the rat deletion mutant readily lysed whereas the complemented strain (ACL2531) behaved like wild-type.

TRITON® X-100 sensitivity was determined for rat, sarA, and rat-sarA double-mutant strains. Both rat and sarA mutants displayed sensitivity to TRITON® X-100 concentrations as low as 0.01%. The double-mutant, however, displayed a more severe defect in TRITON® X-100-induced cell lysis.

Northern blot analysis indicated that rat is transcribed as two transcripts of approximately 560 and 750 nucleotides. Both transcripts are constitutively expressed in wild-type and ALC2012-complemented strains at mid-exponential (OD650 nm=0.7), late-exponential (OD650 nm=1.1) and early-stationary (OD650 nm=1.7) phases of the growth. rat is also expressed in three other strains of S. aureus, 8352–4, Newman, and COL. Furthermore, rat expression is not regulated by other known regulators such as SarR, SarA, SarS, SarT, Agr, or SigB, as rat is expressed at similar levels in wild-type and mutant strains of sarR, sarA, sarS, sarT, agr, sigB, and sarR/agr.

Using standard methodologies, primer extension analysis revealed the transcription start sites of the 567 and 745 nucleotide transcripts. The 567 nucleotide transcript initiated in the context of AATTT*G*TATG (SEQ ID NO:9) located at −124 nucleotides upstream of the translation initiation codon. The 745 nucleotide transcript initiated in the context CAGTC*A*TTGC SEQ ID NO:10) located at −302 nucleotides upstream of the translation initiation codon. Due to the width of the primer extension bands, the transcription initiation site may be at one of the two nucleotides designated by the "*". An 18-bp inverted repeat, located 78-bp downstream of the translation stop codon, is indicative of a transcription termination signal. In the ALC2011 rat mutant, neither transcript is expressed; however, in the ALC2012 complemented strain, both transcripts are present.

Figure 3:
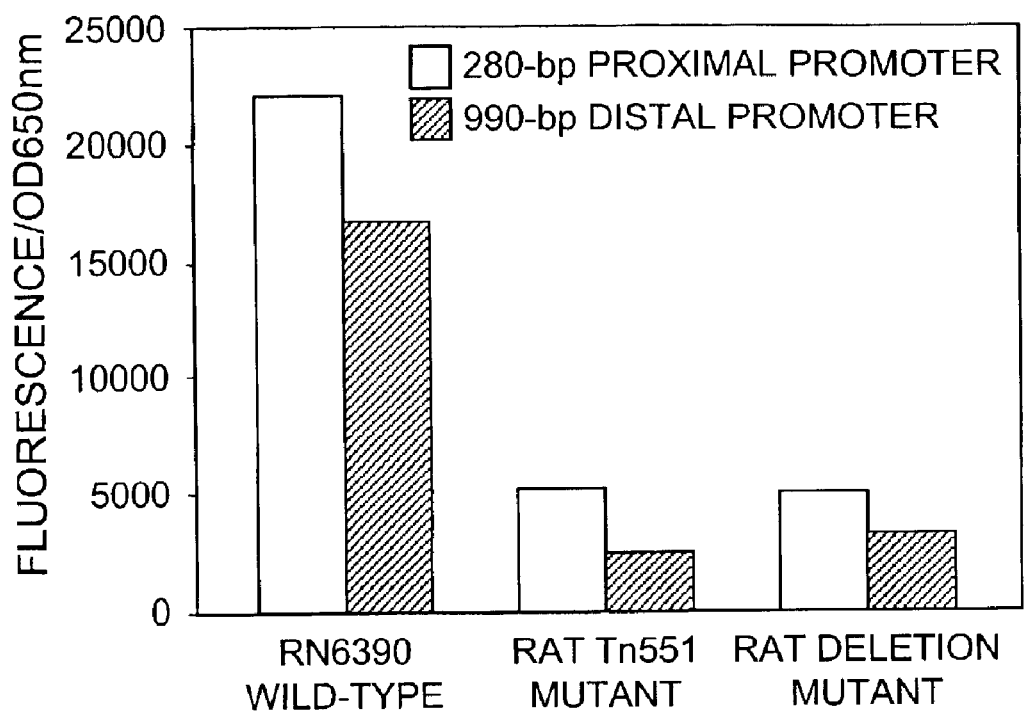
FIG. 3 demonstrates that Rat auto-regulates its own expression.

Expression of rat was determined in wild-type (RN6390) and rat transposon (ALC2529) and deletion mutant (ALC2530) strains of rat. A 280-bp fragment, containing the promoter P1, and a 990-bp fragment encompassing both P1 and P2 promoters of rat were fused to the green fluorescent protein (GFP$_{uvr}$) in shuttle plasmid ALC1484. In both the rat transposon mutant and the rat deletion mutant, there was an ~78–85% reduction in GFP levels attributable to activities for both promoters compared to the wild-type strain (FIG. 3). Both promoters are required for maximum rat expression. These results indicate that either Rat directly autoregulates its own expression or is indirectly regulated by a feed-back loop mechanism.

In a comparison of the deduced Rat polypeptide sequence with polypeptides of other microbes, significant sequence similarity was found between Rat and polypeptides that regulate the expression of multiple antibiotic resistance (MAR) genes in both gram positive and gram negative bacteria (FIG. 4). For example, the Rat polypeptide sequence shares 63%, 61% and 61% sequence similarity with Clostridium acetobutylicum, Bacillus anthracis, and Xanthomonas axonopodis MarR polypeptides, respectively.

Figure 5:
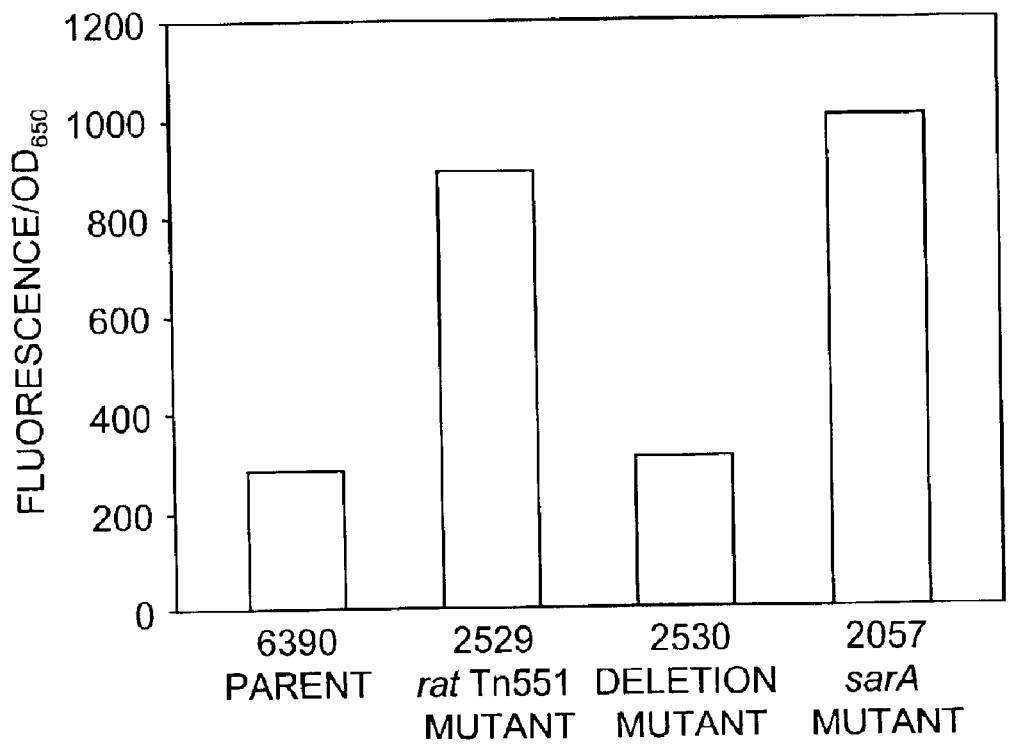
FIG. 5 shows expression of norA-GFP in wild-type (6390), rat transposon mutant (2529), rat deletion mutant (2530), and sarA mutant (2057) strains. Expression is represented as fluorescence per OD unit and was determined for each strain in early stationary phase.
Figure 6:
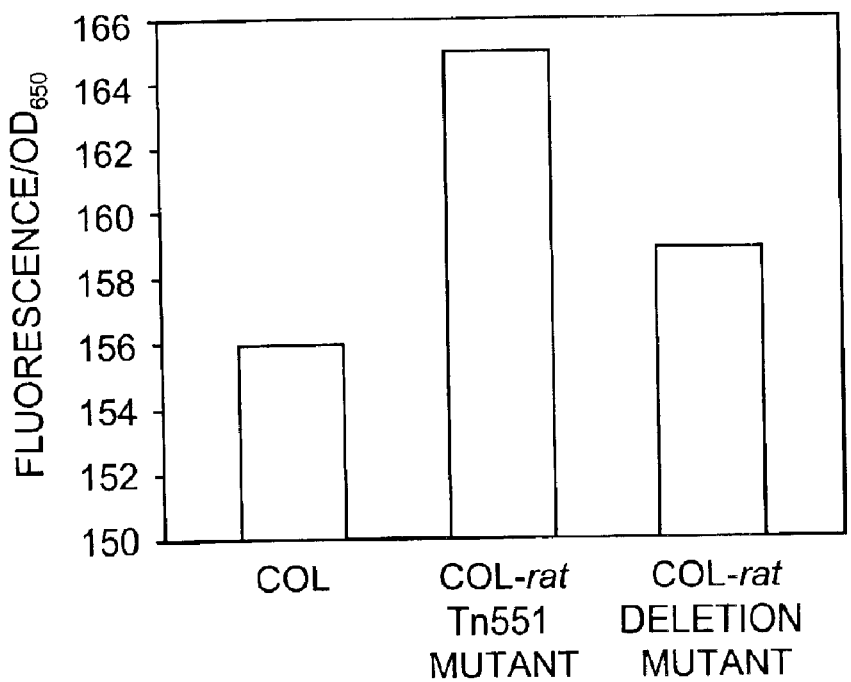
FIG. 6 shows expression of norA-GFP in wild-type MRSA (COL), COL-rat transposon mutant, and COL-rat deletion mutant strains. Expression is represented as fluorescence per OD unit and was determined for each strain in early stationary phase.

In addition to regulating the expression of autolytic enzyme expression, Rat regulates the efflux of antibiotics. The promoter of norA was fused to GFP to demonstrate that Rat polypeptide regulates the expression of norA. The promoter of the norA gene, corresponding to nucleotides 1–471 of accession number D90119, was PCR-amplified using genomic DNA isolated from strain RN6390 as a template. The amplicon was cloned into the KpnI and XbaI restriction sites of pALC1484, a pSK236-based plasmid harboring GFP$_{uvr}$ (Cheung, et al., Infection and Immunity, 1998: 66(12):5988–5993). The resulting norA-GFP expression construct was transformed into wild-type S. aureus strain RN6390, the rat Tn551 transposon mutant of RN6390 (ALC2529), the rat deletion mutant of RN6390 (ALC2530) and a sarA mutant strain as a positive control. GFP fluorescence in the rat transposon mutant and sarA mutant strain was approximately four-fold higher than that in either the wild-type or deletion mutant strain (FIG. 5). Similarly, when the norA-GFP expression construct was transformed into wild-type Staphylococcus aureus MRSA strain COL, a methicillin-resistant strain (de Lencastre and Tomasz, *Antimicrobial Agents and Chemotherapy*, 1994: 38(11): 2590–2598); a rat Tn551 transposon mutant of COL; and a rat deletion mutant of COL, an increase in GFP fluorescence was observed in the rat transposon mutant (FIG. 6). In general, these results demonstrate that a strain deficient in functional Rat polypeptide activity has an increased level of norA gene expression. Therefore, Rat is a negative regulator of norA gene expression.

In a comparison of the nucleic acid sequences encoding Rat with the genomes of other microbes, homologs with significant sequence similarity were identified. Rat or a homolog thereof performs a role in regulating the autolytic activity of bacteria, including but not limited to: *Staphylococcus aureus* (such as *Staphylococcus aureus* N315, *Staphylococcus aureus* strain Mu50, *Staphylococcus aureus* MSSA strain NCTC 8325, *Staphylococcus aureus* MRSA strain COL, *Staphylococcus epidermidis*, and *Staphylococcus sciuri*), *Sinorhizobium* species (e.g., *meliloti*), *Listeria* species (e.g., *monocytogenes*), *Clostridium* species (e.g., *acetabutylicum, difficile*), *Vibrio* species (e.g., *cholerae*), *Corynebacterium* species (e.g., *diptheriae*), *Brucella* species (e.g., *suis*), *Pseudomonas* species (e.g., *aeruginosa, syringae, putida*), *Shewanella* species (e.g., *putrefasciens*), *Mesorhizobium* species (e.g., *loti*), *Caulobacter* species (e.g., *crescentus*), *Lactococcus* species (e.g., *lactis*), *Mycobacterium* species (e.g., *smegmatis, leprae, tuberculosis*), *Burkholderia* species (e.g., *mallei, pseudomallei*), *Geobacter* species (e.g., *sulfurreducens*), *Treponema* species (e.g., *denticola*), *Bacillus* species (e.g., *stearothermophilus, anthracis, subtilis, halodurnas*), *Escherichia* species (e.g., *coli*), *Enterococcus* species (e.g., *faecalis*), *Salmonella* species (e.g., *dublin, enteriditis, paratyphi, typhi*), *Klebsiella* species (e.g., *pneumoniae*), *Bordetella* species (e.g., *parapertussis*), *Actinobacillus* species (e.g., *actinomycetemcomitans*), *Streptomyces* species (e.g., *coelicolor*), *Streptococcus* species (e.g., *pyogenes, pneumoniae*), *Yersinia* species (e.g., *pestis*), *Agrobacterium* species (e.g., *tumefaciens*) and *Acinetobacter* species.

Useful homologous sequences are those which encode a polypeptide which increases bacterial susceptibility to autolysis, increases lysis due to antibiotic administration, or regulates the expression of nucleic acid sequences encoding MAR-associated polypeptides such as norA. In a preferred embodiment the polynucleotide sequence is at least 60 percent homologous to the SEQ SEQ ID NO:1or SEQ ID NO:2. In a more preferred embodiment the polynucleotide sequence is at least 80 percent homologous to the SEQ ID NO:1or SEQ SEQ ID NO:2.

The present invention includes the nucleic acid sequences for the rat gene and rat mutant gene. Exemplary nucleic acid sequences of the present invention are SEQ ID NO:1and SEQ SEQ ID NO:2. However, by the term "nucleic acid sequence" it is meant to include any form of DNA or RNA such as genomic DNA or mRNA, respectively, encoding a Rat polypeptide or Rat mutant polypeptide, or an active fragment thereof which are obtained by cloning or produced synthetically by well-known chemical techniques. DNA may be double- or single-stranded. Single-stranded DNA may comprise the coding or sense strand or the non-coding or antisense strand. Thus, the term nucleic acid sequence also includes sequences which hybridize under stringent conditions to the above-described polynucleotides. As used herein, the term "stringent conditions" means at least 80% homology at hybridization conditions of 60° C. at 2×SSC buffer.

In a preferred embodiment, the nucleic acid sequence comprises the DNA of SEQ ID NO:1or a homologous sequence or fragment thereof. In another preferred embodiment, the nucleic acid sequence comprises the DNA of SEQ SEQ ID NO:2 or a homologous sequence or fragment thereof. Due to the degeneracy of the genetic code, nucleic acid sequences of the present invention also may comprise other nucleic acid sequences encoding the Rat polypeptide or Rat mutant polypeptide and derivatives, variants or active fragments thereof. The present invention also relates to variants of these nucleic acid sequences which may be naturally occurring, i.e., allelic variants, or mutants prepared by well-known mutagenesis techniques.

The present invention also relates to a conditional mutant whereby the rat gene or rat mutant gene may be expressed under an inducible promoter.

The present invention also relates to vectors comprising nucleic acid sequences of the present invention and host cells which are genetically engineered with these vectors to produce active Rat polypeptides or Rat mutant polypeptides, or fragments thereof. Generally, any vector suitable to maintain, propagate or express the nucleic acid sequences of this invention in a host cell may be used for expression in this regard.

The nucleic acid sequences and polypeptides of the present invention, as well as vectors and host cells expressing the polypeptides are useful as research tools to enhance the understanding of the autolytic process of *S. aureus* and other bacteria. The methods and compositions of the present invention are believed to be effective in other bacteria having significant homology with the polynucleotide sequence of rat or the rat mutant.

Further, the rat gene composition is useful in the identification of agents which interact with the rat gene to modulate autolytic activity of the bacteria. By "interact" it is meant that the agent increases or decreases expression of products of nucleic acid sequences encoding Rat. In a preferred embodiment, agents will decrease, interfere with or inhibit the expression of products of nucleic acid sequences encoding Rat so that the bacteria is lysed more easily. Examples of such agents include, but are not limited to, antisense molecules, RNAi or ribozymes targeted to the rat gene which inhibit expression of products of nucleic acid sequences encoding Rat, means for introduction of mutations into the rat gene which inhibit expression of products of nucleic acid sequences encoding Rat or produce a Rat polypeptide with decreased activity, and small organic molecules or peptides which are capable of inhibiting expression of products of nucleic acid sequences encoding Rat themselves (e.g., by binding to the promoter region of the gene to inhibit transcription and subsequent expression). Alternatively, a small compound library may be used to screen for agents which augment the lytic activity of the rat gene.

In another preferred embodiment, agents will increase, activate or stimulate expression of products of nucleic acid sequences encoding Rat to repress, decrease, or inhibit the expression of products of nucleic acid sequences encoding multiple antibiotic resistance polypeptides so that the efflux of antibiotics is reduced or prevented. Examples of such agents include, but are not limited to, means for introduction of mutations into the rat gene which stimulate expression of products of nucleic acid sequences encoding Rat and small organic molecules or peptides which are capable of increasing or stimulating expression of products of nucleic acid sequences encoding Rat themselves (e.g., by binding to the promoter region of the gene to promote transcription and subsequent expression).

Accordingly, the invention provides a method for identifying agents that modulate cell lysis in bacteria. The method provides contacting a test cell, which contains a reporter gene operably linked to a rat promoter, with an agent and then detecting the expression of products of nucleic acid sequences encoding the reporter in the test cell. An agent which causes an increase or decrease in expression of products of nucleic acid sequences encoding the reporter in the test cell when compared a test cell not contacted with the agent, indicates that the agent modulates cell lysis in the test cell.

The test cells of the invention are employed in screening assays for the identification of agents that modulate cell lysis. Test cells expressing a products of nucleic acids encoding a reporter which may be used in accordance with the invention include, but are not limited to, bacteria such as *E. coli* and *S. aureus*. Furthermore, such test cells may be wild-type cells or cells which contain a mutation in rat which does not alter auto-regulation of Rat.

The reporter gene sequence(s) may be inserted into a recombinant expression vector. A reporter gene construct refers to a plasmid, virus or other vehicle known in the art that has been manipulated by insertion or incorporation of nucleic acid sequences encoding a reporter. Such reporter gene constructs of the invention are preferably plasmids which contain a rat promoter sequence which is operably associated with the inserted nucleic acid sequences encoding the reporter. It typically contains an origin of replication as well as specific genes which allow phenotypic selection of the transformed cells.

A promoter which is operably associated or operably linked to nucleic acid sequences encoding a reporter means that the sequences are joined and positioned in such a way as to permit transcription. Two or more sequences, such as a promoter and any other nucleic acid sequences are operably associated if transcription commencing in the promoter will produce an RNA transcript of the operably associated sequences.

Various promoter sequences may be generated by PCR using genomic DNA or plasmid DNA containing SEQ SEQ ID NO:1 or SEQ SEQ ID NO:2 as templates. Primers may be synthesized corresponding to the 5' and 3' boundaries of the selected promoter regions. Primers also may contain additional restriction enzyme recognition sequences to facilitate subcloning. It is preferred that the promoter region is a 280-bp fragment of SEQ ID NO:1or SEQ ID NO:2 with a 3' boundary at the translation start site. It is more preferred that promoter region is a 990-bp fragment of SEQ ID NO:1or SEQ ID NO:2 with a 3' boundary at the translation start site.

A reporter gene construct useful in the invention also may contain selectable or screenable marker genes for initially isolating, identifying or tracking test cells that contain heterologous DNA. The reporter gene construct also may provide unique or conveniently located restriction sites to allow severing and/or rearranging portions of the DNA inserts in a reporter gene construct. More than one reporter gene may be inserted into the construct such that the test cells containing the resulting construct may be assayed by different means.

Introduction of the reporter gene construct into the DNA of bacterial cells may be carried out by conventional techniques well-known to those skilled in the art, such as transformation, conjugation, and transduction.

In addition to conventional chemical methods of transformation, the plasmid vectors of the invention may be introduced into a host cell by physical means, such as by electroporation or microinjection. Electroporation allows transfer of the vector by high voltage electric impulse, which creates pores in the plasma membrane of the host and is performed according to methods well known in the art. Additionally, cloned DNA can be introduced into test cells by protoplast fusion, using methods well-known in the art. The reporter gene construct may be introduced into a test cell transiently, or more typically, the nucleic acids are stably integrated into the genome of the test cell or remain as stable episomes in the test cell.

The test cells which contain the nucleic acid sequences encoding the reporter and which express products of the nucleic acid sequences encoding the reporter may be identified by at least four general approaches; detecting DNA-DNA or DNA-RNA hybridization; observing the presence or absence of marker gene functions (e.g., resistance to antibiotics); assessing the level of transcription as measured by the expression of reporter mRNA transcripts in the host cell; and detecting the reporter gene product as measured by immunoassay or by its biological activity.

The test cells may be cultured under standard conditions of temperature, incubation time, optical density, plating density and media composition corresponding to the nutritional and physiological requirements of the bacteria. However, conditions for maintenance and growth of the test cell may be different from those for assaying candidate test compounds in the screening methods of the invention. Modified culture conditions and media are used to facilitate detection of the expression of a reporter molecule. Any techniques known in the art may be applied to establish the optimal conditions.

A reporter gene refers to any genetic sequence that is detectable and distinguishable from other genetic sequences present in test cells. Preferably, the reporter nucleic acid sequence encodes a protein that is readily detectable either by its presence, or by its activity that results in the generation of a detectable signal. A nucleic acid sequences encoding the reporter are used in the invention to monitor and report the activity of a rat promoter in test cells.

A variety of enzymes may be used as reporters including, but are not limited to, β-galactosidase (Nolan et al. *Proc. Natl. Acad. Sci. USA,* 1988: 85:2603–2607), chloramphenicol acetyltransferase (CAT; Gorman et al., *Molecular Cell Biology,* 1982: 2:1044; Prost et al., *Gene,* 1986: 45:107–111), β-lactamase, β-glucuronidase and alkaline phosphatase (Berger et al., *Gene,* 1988: 66:1–10; Cullen et al., *Methods Enzymol,* 1992: 216:362–368). Transcription of the reporter gene leads to production of the enzyme in test cells. The amount of enzyme present may be measured via its enzymatic action on a substrate resulting in the formation of a detectable reaction product. The methods of the invention provide means for determining the amount of reaction product, wherein the amount of reaction product generated or the remaining amount of substrate is related to the amount of enzyme activity. For some enzymes, such as β-galactosidase, β-glucuronidase and β-lactamase, well-known fluorogenic substrates are available that allow the enzyme to covert such substrates into detectable fluorescent products.

A variety of bioluminescent, chemiluminescent and fluorescent proteins also may be used as light-emitting reporters in the invention. Exemplary light-emitting reporters, which are enzymes and require cofactor(s) to emit light, include, but are not limited to, the bacterial luciferase (luxAB gene product) of *Vibrio harveyi* (Karp, *Biochim. Biophys. Acta,*

1989: 1007:84–90; Stewart et al., *Journal of General Microbiology*, 1992: 138:1289–1300), and the luciferase from firefly, *Photinus pyralis* (De Wet et al., *Mol. Cell. Biol.*, 1987: 7:725–737).

Another type of light-emitting reporter, which does not require substrates or cofactors includes, but is not limited to, the wild-type green fluorescent protein (GFP) of *Victoria aequoria* (Chalfie et al., *Science*, 1994: 263:802–805), modified GFPs (Heim et al., *Nature*, 1995: 373:663–4; WO 96/23810), and the gene products encoded by the *Photorhabdus luminescens* lux operon (luxABCDE) (Francis, et al., *Infection & Immunity*, 2000:68(6):3594–600). Transcription and translation of these type of reporter genes leads to the accumulation of the fluorescent or bioluminescent proteins in test cells, which may be measured by a device, such as a fluorimeter, flow cytometer, or luminometer. Methods for performing assays on fluorescent materials are well-known in the art (e.g., Lackowicz, J. R., 1983, *Principles of Fluorescence Spectroscopy*, New York:Plenum Press).

For convenience and efficiency, enzymatic reporters and light-emitting reporters are preferred for the screening assays of the invention. Accordingly, the invention encompasses histochemical, calorimetric and fluorometric assays. An exemplary reporter construct, provided herein, contains the rat promoter which regulates the transcription and translation (expression) of the reporter, GFP.

Accordingly, the invention provides a method for screening for agents that modulate cell lysis of bacteria comprising culturing a test cell which contains nucleic acid sequences encoding a reporter operably linked to the rat promoter; adding a test agent to a point of application, such as a well, in the plate and incubating the plate for a time sufficient to allow the test agent to effect GFP accumulation; detecting fluorescence and growth of the test cells contacted with the test agent, wherein fluorescence indicates expression of the GFP polypeptide in the test cells; and comparing the fluorescence and growth of test cells not contacted with the test agent. A decrease in fluorescence and growth of the test cell contacting the test agent relative to the fluorescence and growth of test cells not contacting the test agent indicates that the test agent causes a decrease in expression of products of nucleic acid sequences encoding Rat in the test cell. An increase in fluorescence and decrease in growth of the test cell contacting the test agent relative to the fluorescence and growth of test cells not contacting the test agent indicates that the test agent causes an increase in expression of products of nucleic acid sequences encoding Rat in the test cell.

Hence, one aspect of the present invention provides an analog library to produce a very large number of potential molecules or agents for regulating the expression of products of nucleic acid sequences encoding Rat, and in general the greater the number of analogs in the library, the greater the likelihood that at least one member of the library will effectively regulate the expression of products of nucleic acid sequences encoding Rat. Designed libraries following a particular template structure and limiting amino acid variation at particular positions are much preferred, since a single library may encompass all the designed analogs and the included sequences will be known and presented in roughly equal numbers. By contrast, random substitution at only six positions in an amino acid sequence provides over 60 million analogs, which is a library size that begins to present practical limitations even when utilizing screening techniques as powerful as phage display. Libraries larger than this would pose problems in handling, e.g., fermentation vessels would need to be of extraordinary size, and more importantly, the likelihood of having all of the planned polypeptide sequence variations represented in the prepared library would decrease sharply. It is therefore preferred to create a designed or biased library, in which the amino acid positions designated for variation are considered so as to maximize the effect of substitution on the Rat regulation characteristics of the analog, and the amino acid residues allowed or planned for use in substitutions are limited.

The use of replicable genetic packages, such as the bacteriophages, is one method of generating novel polypeptide entities that regulate the expression of products of nucleic acid sequences encoding Rat. This method generally consists of introducing a novel, exogenous DNA segment into the genome of a bacteriophage (or other amplifiable genetic package) so that the polypeptide encoded by the non-native DNA appears on the surface of the phage. When the inserted DNA contains sequence diversity, then each recipient phage displays one variant of the template amino acid sequence encoded by the DNA, and the phage population (library) displays a vast number of different but related amino acid sequences.

Such techniques make it possible not only to screen a large number of potential binding molecules but make it practical to repeat the binding/elution cycles and to build secondary, biased libraries for screening analog-displaying packages that meet the initial criteria.

It is well-known to those skilled in the art that it is possible to replace peptides with peptidomimetics. Peptidomimetics are generally preferable as therapeutic agents to peptides owing to their enhanced bioavailability and relative lack of attack from proteolytic enzymes. Accordingly, the present invention also provides peptidomimetics and other lead compounds which may be identified based on data obtained from structural analysis of Rat. A potential analog may be examined through the use of computer modeling using a docking program such as GRAM, DOCK, or AUTODOCK. This procedure may include computer fitting of potential analogs. Computer programs also may be employed to estimate the attraction, repulsion, and steric hindrance of an analog to a potential binding site. Generally the tighter the fit (e.g., the lower the steric hindrance, and/or the greater the attractive force) the more potent the potential analog will be since these properties are consistent with a tighter binding constant. Furthermore, the more specificity in the design of a potential analog the more likely that the analog will not interfere with other properties of the expression of rat. This will minimize potential side-effects due to unwanted interactions with other proteins.

Initially a potential analog could be obtained by screening a random peptide library produced by a recombinant bacteriophage, for example, or a chemical library. An analog ligand selected in this manner could then be systematically modified by computer modeling programs until one or more promising potential ligands are identified.

Such computer modeling allows the selection of a finite number of rational chemical modifications, as opposed to the countless number of essentially random chemical modifications that could be made, and of which any one might lead to a useful agent. Thus, the three-dimensional structure and computer modeling, provides that a large number of agents may be rapidly screened and a few likely candidates may be determined without the laborious synthesis of untold numbers of agents.

Once a potential peptidomimetic or lead compound is identified it may be either selected from a library of chemicals commercially available from most large chemical companies including Merck, GlaxoWelcome, Bristol Meyers Squibb, Monsanto/Searle, Eli Lilly, Novartis and Pharmacia UpJohn, or alternatively the potential ligand is synthesized de novo. As mentioned above, the de novo synthesis of one or even a relatively small group of specific compounds is reasonable in the art of designing compounds.

Accordingly, the present invention provides agents identified as inhibitors of expression of products of nucleic acid sequences encoding Rat and methods for using these agents to increase lysis of S. aureus and other bacteria, thereby inhibiting their growth and infectivity. Furthermore, the invention provides agents identified as stimulators or activators of expression of products of nucleic acid sequences encoding Rat and methods for using these agents to decrease, repress, or inhibit multiple antibiotic resistance gene expression of S. aureus and other bacteria, thereby preventing or reducing bacterial resistance to antimicrobial agents. These agents may be incorporated into a pharmaceutical composition and administered to a host to inhibit growth and infectivity of S. aureus and other bacteria in the host. The term "host" as used herein includes humans.

Pharmaceutical compositions of the present invention comprise an effective amount of an agent which alters the expression of a product of a nucleic acid sequence encoding Rat and a pharmaceutically acceptable vehicle. Such pharmaceutical compositions may be prepared by methods and contain vehicles which are well-known in the art. A generally recognized compendium of such methods and ingredients is Remington's Pharmaceutical Sciences (A. R. Gennaro ed. 1985. Mack Publishing Co.). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

By "effective amount" it is meant an amount which inactivates the expression of a product of a nucleic acid sequence encoding Rat and renders S. aureus or other bacteria susceptible to killing through cell lysis. Alternatively, an effective amount may be an amount which activates the expression of a product of a nucleic acid sequence encoding Rat and renders S. aureus or other bacteria susceptible to antibiotic killing through prevention or reduction of multidrug resistance transporter protein expression. The pharmaceutical compositions may be administered to a host, preferably a human, to inhibit the growth of S. aureus or other bacteria in the host.

The pharmaceutical composition may be administered alone, or in combination with an antibiotic such as a penicillin (e.g., penicillin, ampicillin, carbenicillin, methicillin, oxacillin), a penam (e.g., imipenem), a cephalosporin (e.g., cephalothin, cefoxitin, cefotaxime), an aminoglycoside (e.g., gentamicin, kanamycin, tobramycin, amikacin, streptomycin, neomycin), a tetracycline (e.g., tetracycline, doxycycline), a macrolide (e.g., erythromycin, clarithromycin, azithromycin), a quinolone (e.g., ciprofloxacin, gatifloxacin, levofloxacin), rifampin or vancomycin to enhance killing or lysis of the bacteria. Furthermore, the pharmaceutical compositions may be administered in combination with known multidrug resistance pump inhibitors such as 5'-methoxyhydnocarpin-D and pheophorbide A. Pharmaceutical compositions of the present invention may be administered by various routes, including, but not limited to, topically, intramuscularly, intraperitoneally, intranasally, orally, subcutaneously, or intravenously.

The present invention also provides a pharmaceutical pack or kit comprising one or more containers filled with one or more of the ingredients of the agents or pharmaceutical compositions of the invention. The kit may be used for identifying the presence of a rat gene in a biological sample by analyzing the sample for the presence of rat. Detection of rat cells in a sample are indicative of the patient being susceptible to treatment for the bacterial infection using conventional antibiotic treatment, such as penicillin. Associated with such container(s) may be a notice in the form of prescribed by a governmental agency regulating the manufacture, use or sale of pharmaceuticals or biological products, which notice reflects approval by the agency or manufacture, use or sale for human administration.

The embodiments herein described are not meant to be limiting to the invention. Those of skill in the art will appreciate the invention may be practiced by using numerous chemical entities and by numerous methods all within the breadth of the following claims.

EXAMPLE 1

Bacterial Strains, Plasmids and Growth Conditions

Phage φ11 and 80α were used as the transducing phage for S. aureus strains. S. aureus cells were grown at 37° C. with aeration in CYGP or O3GL broth or Tryptic soy broth (TSB) supplemented with antibiotics when necessary. Luria-Bertani (LB) broth was used for cultivating E. coli Antibiotics were used at the following concentrations for S. aureus: erythromycin, 5 μg/ml; tetracycline, 3 μg/ml; chloramphenicol, 10 μg/ml; kanamycin, 50 μg/ml; for E. coli ampicillin, 50 μg/ml; spectinomycin, 75 μg/ml.

EXAMPLE 2

Genetic Manipulations in E. coli and S. aureus

Recombinant plasmid construction was performed in E. coli DH5α™. Standard molecular biology and recombinant DNA techniques were used (Sambrook et al. (1989) *Molecular Cloning, a Laboratory Manual*, Cold Spring Harbor Laboratories, New York).

S. aureus strain RN4220, a restriction deficient derivative of strain 8325–4, was used as the initial recipient for the transformation of plasmid constructs, using well-known electroporation methods.

A Tn551 transposon library was constructed in RN6390 (Cheung, et al., *Journal of Bacteriology*, 1995: 177(11):3220–6), using the temperature-sensitive plasmid pI258 as the delivery vehicle for the transposon. A reporter plasmid containing the cap5 promoter driving the promoterless gfp$_{uvr}$ was electroporated into the transposon library to select for mutants that had decreased GFP fluorescence. One mutant, ALC2011, had a defect in autolytic activities.

To construct a rat deletion mutant, upstream and downstream sequences flanking the rat open reading frame were PCR-amplified, using RN6390 chromosomal DNA as a template. PCR primers used for amplification of the upstream fragment were 5'-CGA GAG CTC TAA ATG ACA CAT AAC CTT TCA-3' SEQ ID NO:11) and 5'-TCC CCC GGG ATT GGT AAT CAT TAA AAA GTT-3' SEQ ID NO:12), and for downstream fragment 5'-CCG GTC GAC CTT GAT TAG CTA GTA ATT GTT-3' (SEQ SEQ ID NO:13) and 5'-AAC TGC AGC GCT AGT TAC AGT CAT AGT TT-3' SEQ ID NO:14). The upstream fragment was cloned into SmaI-SacI and the downstream into SalI-PstI sites of the temperature-sensitive shuttle vector pCL52.2. The antibiotic marker ermC (1.2-kb fragment) was inserted between these two fragments such that the ermC gene was divergent from the rat gene. This recombinant plasmid (pALC2463) was used to transform RN4220. Transformants were selected for erythromycin resistant colonies at 30° C. The recombinant plasmid was isolated from RN4220 and introduced into RN6390 by electroporation. *S. aureus* strain RN6390, harboring plasmid pALC2463, was grown overnight at 30° C. in TSB to allow plasmid replication and propagated at 42° C., a non-permissive temperature for replication of pCL52.2. This cycle was repeated 4–5 times and cells were plated on O3GL plates containing erythromycin or erythromycin and tetracycline to select for tetracycline sensitive and erythromycin resistant colonies, representing mutants with double-crossovers. After six cycles, putative mutants were obtained. PCR and Southern blot analysis confirmed the double-crossover events. One clone, designated ALC2530, was further analyzed.

To complement the rat mutation, a 3.2-kb rat fragment was amplified from RN6390 DNA with primers 5'-CGA GAG CTC TAA ATG ACA CAT AAC CTT TCA-3' SEQ ID NO:15) and 5'-AAC TGC AGC GCT AGT TAC AGT CAT AGT TT-3' SEQ ID NO:16) and cloned into pCL84, a plasmid that integrates into the lipase gene of *S. aureus* (Lee, et al., *Gene*, 1991: 103:101–105.), to yield pALC2464. CLY316, an RN4420 derivative, was transformed with pALC2464 and tetracycline resistant colonies were selected. For correct chromosomal integration, colonies were checked for negative lipase activity on egg-yolk agar plates. The integrated plasmid containing the complete rat gene in RN4220 was transduced into the rat transposon (ALC2529) and deletion (ALC2530) mutant strains, using phage Φ11. Tetracycline resistance strains lacking lipase activity were analyzed for the complementation phenotype.

To generate other rat transposon and rat deletion mutants, φ11 and 80α phage lysates of ALC2529 and ALC2530 were used to infect 8325–4, COL, Newman, ALC2057 (sarA mutant), RN6911 (agr mutant) and ALC2538 (sarA/agr double mutant) strains.

EXAMPLE 3
Zymographic Analysis

Cell-associated murein hydrolase activity was detected using SDS-PAGE zymographic analysis. Briefly, an equal number of cells from each strain were centrifuged, washed and resuspended in SDS-gel loading buffer, heated for three minutes at 100° C., and centrifuged to obtain supernatant. Supernatants were separated on a 12% SDS-polyacrylamide gel containing RN4220 cells (1 mg wet weight per ml, heat-killed). After electrophoresis, gels were washed with water and incubated for 12 hours in 25 mM Tris-HCl (pH 8.0) containing 1% TRITON® X-100 at 37° C. Gels were stained with 1% methylene blue and clear zones of hydrolysis were observed against a dark background.

EXAMPLE 4
Transmission Electron Microscopy

Bacterial cells in the mid-exponential phase of growth were washed four times with PBS and then fixed with 2% gluteraldehyde/1% paraformaldehyde in 0.1 M sodium cacodylate, pH 7.4, overnight. The cells were washed three times with 0.1 M sodium cacodylate, pH 7.4. The cells were then suspended in 1% $OsO_4$ in 0.1 M sodium cacodylate, pH 7.4, for one hour at room temperature and subsequently rinsed with 0.1 M sodium cacodylate, pH 7.4, and distilled water. En bloc stain: 1–2% Uranyl Acetateaq for 30 minutes at room temperature, in the dark. The cells were rinsed with water and dehydrated in a series of ethanol washes. Prior to fixing, the cells were washed twice with propylene oxide. The pellet was immersed in LX112:PO (1.5:1). Vials were capped for two hours. Caps were removed and the vials were desiccated overnight under vacuum. Cellular pellets were then transferred to the BEEM capsule and filled with fresh LX112. The solution was centrifuged for 30 minutes at 1,000 rpm to pellet cells to the bottom of the capsule. Cells were desiccated overnight under vacuum and subsequently cut in thin sections and stained with 1% uranyl acetate.

EXAMPLE 5
Autolytic Assays

The effect of TRITON® X-100 on growing cells was determined by diluting cultures grown overnight to an OD650 nm of 0.1 in TSB with varying concentrations of TRITON® X-100. Cells were incubated at 37° C. with shaking and the optical density was recorded hourly for seven to eight hours.

TRITON® X-100-induced autolysis assays were conducted by diluting cultures grown overnight to an OD650 nm of 0.05 in TSB containing 1 M NaCl. Cells were allowed to grow at 37° C. with shaking until an OD650 nm of 0.7 was reached. Cells were harvested, washed twice with ice cold water and then resuspended in the same volume of 0.05 M Tris-HCl, pH 7.2, containing 0.05% TRITON® X-100. Cells were incubated at 30° C. with shaking and lysis was determined by measuring absorbance at OD600 nm at 30 minutes intervals.

Penicillin sensitivity assays were conducted by diluting rat mutant cultures grown overnight to an OD650 nm of 0.05 in TSB containing the appropriate antibiotics to maintain selection. Cultures were grown at 37° C. with shaking to reach exponential phase (OD650 nm=0.5). Penicillin G was added to a concentration of 0.1 µg/ml. Optical densities at 650 nm were measured every hour for eight to nine hours.

EXAMPLE 6
RNA Isolation, Northern Blot Analysis and Primer Extension

Overnight cultures of *S. aureus* were diluted 1:100 in CYGP and grown to mid-log (OD650 nm=0.7), late-log (OD650 nm=1.1), and early stationary (OD650 nm=1.7) phases. The cells were harvested and processed with a TRIZOL™ isolation kit (Gibco BRL, Gaithersburg, Md.) in combination with 0.1-mm-diameter sirconia-silica beads in a reciprocating shaker (Biospec, Inc. Bartlesville, Okla.). Fifteen micrograms of each sample was electrophoresed in a 1.5% agarose-0.66 M formaldehyde gel in morpholinepropanesulfonic acid (MOPS) running buffer (20 mM MOPS, 10 mM sodium acetate, 2 mM EDTA, pH 7.0). Northern blotting of RNA was performed with the TURBOBLOTTER™ alkaline transfer system (Schleicher & Schuell, Keene, N.H.) onto HYBOND™ N⁺ membranes (AMERSHAM™, Arlington Heights, Ill.). For detecting lytSR, lrgAB, arlRS, lytM, lytN, atl, pbp2, pbp4, abcA, sspA, agr, sarA, sarR, sarS, sarT, spa, scdA, hla and rat, gel-purified DNA probes were radiolabeled with $\alpha$-$^{32}$P dCTP by a random-primed DNA labeling kit (Roche Diagnostics GmbH, Mannheim, GER) and hybridized under aqueous phase conditions at 65° C. The blots were subsequently washed and exposed to autoradiography film using methods well-known to one of skill in the art.

Primer extension analysis was conducted to map the 5'-end of the rat gene. Primer extension was performed with a synthetic oligonucleotide 5'-CGGGATCCAGACATTAAAGTTCTCCTCCAGA-3' SEQ ID NO:17) (nucleotides +1 to −26). The primer was end-labeled with [$\alpha$-$^{32}$P]-ATP and purified by SEPHADEX® G-25 spin columns (AMERSHAM™ PHARMACIA™ Biotech, Uppsala, Sweden). DNA-free, total RNA (30 µg) was co-precipitated with the end-labeled primer (5×10⁴ dpm) and annealed overnight at 35° C. The reaction mixture was ethanol-precipitated, washed with 70% ethanol, and dried. Reverse transcription was carried out using SUPERSCRIPT II™ (Gibco-BRL, Gaithersburg, Md.) at 42° C. for 90 minutes. Enzyme inactivation was conducted by heating the reaction mixture to 65° C. for 10 minutes. The reaction product was incubated with RNase H (2U) for 15 minutes at 55° C., ethanol precipitated, resuspended in 10 µl of SEQUENASE™ stop solution, denatured and applied to a 4% sequencing gel. Sequencing reaction mixtures, primed with an oligonucleotide identical to that used for primer extension, were applied in parallel lanes on the gel.

EXAMPLE 7

GFP$_{uvr}$ Reporter Constructs

Promoter activities of the regulators of autolysis (lytSR, lrgAB, arlRS) and other genes such as atl and sspA were analyzed using GFP fusions. Promoter fragments of these genes were cloned into the shuttle vector pALC1484, which is a derivative of pSK236, containing the promoterless gfp$_{uvr}$ gene. Transcriptional fusions to the gfp$_{uvr}$ reporter gene were thus created. Restriction analysis and DNA sequencing confirmed the orientation and authenticity of the promoter fragments. Recombinant plasmids were first introduced into *S. aureus* strain RN4220 by electroporation. Plasmids purified from RN4220 transformants were then electroporated into RN6390 and isogenic rat mutants.

Overnight cultures of *S. aureus* strains harboring the recombinant plasmids were diluted 1:100 and grown at 37° C. with shaking in tryptic soy broth containing chloramphenicol (10 µg/ml). Aliquots (200 µl) were transferred hourly to microtiter plates to assay for cell density (OD650 nm) and fluorescence for 10 hour in a FL600 fluorescence reader (BioTek Instrument, Winooski, Vt.). Promoter activation was plotted as mean fluorescence/OD650 nm ratio, using the average values from triplicate readings.

What is claimed is:

1. An isolated nucleic acid encoding a polypeptide which regulates expression of polypeptides involved in autolytic processes in a bacterium, wherein the nucleic acid hybridizes under stringent conditions to a nucleic acid comprising the nucleic acid sequence of SEQ ID NO:1 or SEQ ID NO:2.

2. The nucleic acid of claim 1 wherein the bacterium is *Staphylococus aureus*.

3. The nucleic acid of claim 1 wherein the bacterium comprises *Staphylococcus, Sinorhizobium, Listeria, Clostridium, Bacillus, Corynebacterium, Brucella, Pseudomonas, Shewanella, Mesorhizobium, Caulobacter, Lactococus, Mycobacterium, Burkholderia, Geobacter, Treponema, Vibrio, Escherichia, Enterococcus, Salmonella, Klebsiella, Agrobacterium, Yersinia, Bordetella, Actinobacillus, Streptomyces, Streptococcus,* or *Acinetobacter*.

4. A An isolated nucleic acid comprising the nucleic acid sequence of SEQ ID NO:1 or SEQ ID NO:2.

5. A vector comprising the nucleic acid of claim 1.

6. A host cell comprising the vector of claim 5.

* * * * *

SEQUENCE LISTING

<160> NUMBER OF SEQ ID NOS: 17

<210> SEQ ID NO 1
<211> LENGTH: 950
<212> TYPE: DNA
<213> ORGANISM: Staphylococcus aureus

<400> SEQUENCE: 1

```
taccgaattc attcatgatg attttaattt tctcatcatt ttttaataat tcactaatat      60
aatgtgtcag taacgtggtt ttaccactac ccaaaaatcc gttaattatg gatattctta     120
ttttttcatc tttattattt ttcattttat attctctttt ctattacagt tattttaaa     180 aatgataaca tatatattaa attatctttt tgcttgattt aatcaaaaat atcttctaaa     240 cttttaaacat actttaattt tagcatggca ttgaatcaaa gaaagttgtg aattaataaa     300
caatcaactt tttaatgatt accaatccga aaagagaaaa aaacggatag tatgtctgga     360
ggagaacttt aatgtctgat caacataatt taaaagaaca gctatgcttt agtttgtaca     420
atgctcaaag acaagttaat cgctactact ctaacaaagt ttttaagaag tacaatctaa     480
catacccaca atttcttgtc ttaacaattt tatgggatga atctcctgta aacgtcaaga     540
aagtcgtaac tgaattagca ctcgatactg gtacagtatc accattatta aaacgaatgg     600
aacaagtaga cttaattaag cgtgaacgtt ccgaagtcga tcaacgtgaa gtatttattc     660
acttgactga caaaagtgaa actattagac cagaattaag taatgcatct gacaaagtcg     720
cttcagcttc ttctttatcg caagatgaag ttaaagaact taatcgctta ttaggtaaag     780
tcattcatgc atttgatgaa acaaaggaaa aataattttg tcatgacaat taaagtaatg     840
tttagaattt attaagaata gaaaaacaat tagcacgcgt aagcttgtta gttaaaaaac     900
tgcttgaaag gtttcttagc ctatcaagca gttttttttat gcattatatt                950
```

<210> SEQ ID NO 2
<211> LENGTH: 773
<212> TYPE: DNA
<213> ORGANISM: Staphylococcus aureus

<400> SEQUENCE: 2

```
taccgaattc attcatgatg attttaattt tctcatcatt ttttaataat tcactaatat      60
aatgtgtcag taacgtggtt ttaccactac ccaaaaatcc gttaattatg gatattctta     120
```

-continued

```
tttttttcatc tttattattt ttcattttat attctctttt ctattacagt tatttttaaa      180
aatgataaca tatatattaa attatctttt tgcttgattt aatcaaaaat atcttctaaa      240
ctttaaacat actttaattt tagcatggca ttgaatcaaa gaaagttgtg aattaataaa      300
caatcaactt tttaatgatt accaatccga aaagagaaaa aaacggatag tatgtctgga      360
ggagaacttt aatgtctgat caacataatt taaaagaaca gctatgcttt agtttgtaca      420
atgctcaaag acaagttaat cgctactact ctaacaaagt ttttaagaag tacaatctaa      480
catacccaca atttcttgtc ttaacaattt tatgggatga atctcctgta aacgtcaaga      540
aagtcgtaac tgaattagca ctcgatactg gtacagtatc accattatta aaacgaatgg      600
aacaagtaga cttaattaag cgtgaacgtt ccgaagtcga tcaacgtgaa gtatttattc      660
acttgactga caaaagtgaa actattagac cagaattaag taatgcatct gacaaagtcg      720
cttcagcttc ttctttatcg caagatgaag ttaaagaact taatcgctta tta            773
```

<210> SEQ ID NO 3
<211> LENGTH: 147
<212> TYPE: PRT
<213> ORGANISM: Staphylococcus aureus

<400> SEQUENCE: 3

```
Met Ser Asp Gln His Asn Leu Lys Glu Gln Leu Cys Phe Ser Leu Tyr
 1               5                  10                  15

Asn Ala Gln Arg Gln Val Asn Arg Tyr Tyr Ser Asn Lys Val Phe Lys
            20                  25                  30

Lys Tyr Asn Leu Thr Tyr Pro Gln Phe Leu Val Leu Thr Ile Leu Trp
        35                  40                  45

Asp Glu Ser Pro Val Asn Val Lys Lys Val Val Thr Glu Leu Ala Leu
    50                  55                  60

Asp Thr Gly Thr Val Ser Pro Leu Leu Lys Arg Met Glu Gln Val Asp
65                  70                  75                  80

Leu Ile Lys Arg Glu Arg Ser Glu Val Asp Gln Arg Glu Val Phe Ile
                85                  90                  95

His Leu Thr Asp Lys Ser Glu Thr Ile Arg Pro Glu Leu Ser Asn Ala
            100                 105                 110

Ser Asp Lys Val Ala Ser Ala Ser Ser Leu Ser Gln Asp Glu Val Lys
        115                 120                 125

Glu Leu Asn Arg Leu Leu Gly Lys Val Ile His Ala Phe Asp Glu Thr
    130                 135                 140

Lys Glu Lys
145
```

<210> SEQ ID NO 4
<211> LENGTH: 150
<212> TYPE: PRT
<213> ORGANISM: Bacillus anthracis

<400> SEQUENCE: 4

```
Met Thr Glu Asp Ser Leu His Leu Asp Asn Gln Leu Cys Phe Ser Ile
 1               5                  10                  15

Tyr Ala Cys Ser Arg Glu Val Thr Arg Phe Tyr Arg Pro Tyr Leu Glu
            20                  25                  30

Glu Met Gly Ile Thr Tyr Pro Gln Tyr Ile Thr Leu Val Leu Trp
        35                  40                  45

Glu Gln Asp Gly Leu Thr Val Lys Glu Ile Gly Glu Arg Leu Phe Leu
    50                  55                  60
```

-continued

```
Asp Ser Gly Thr Leu Thr Pro Met Leu Lys Arg Met Glu Ser Leu Asn
65                  70                  75                  80

Leu Val Lys Arg Val Arg Ser Lys Glu Asp Glu Arg Lys Val Cys Ile
                85                  90                  95

Glu Leu Thr Glu Gln Gly Lys Asp Leu Gln Asp Lys Ala Cys Ser Leu
            100                 105                 110

Pro Thr Thr Met Ala Thr Asn Leu Gly Ile Thr Glu Gln Glu Tyr Arg
        115                 120                 125

Ser Leu Leu Ile Gln Leu Asn Lys Leu Ile Glu Thr Met Lys Thr Ile
    130                 135                 140

Asn Asp Arg Lys Gly Glu
145                 150

<210> SEQ ID NO 5
<211> LENGTH: 143
<212> TYPE: PRT
<213> ORGANISM: Clostridium acetobutylicum

<400> SEQUENCE: 5

Met Gln Asp Gly Glu Gln Leu Lys Leu Lys Tyr Gln Leu Cys Phe Ser
1               5                   10                  15

Ile Tyr Ala Ser Ser Arg Ala Ile Thr Lys Val Tyr Lys Pro Phe Leu
            20                  25                  30

Asn Lys Leu Gly Leu Thr Tyr Pro Gln Tyr Leu Val Met Leu Val Leu
        35                  40                  45

Trp Glu Glu Lys Ser Ile Thr Leu Lys Asp Leu Gly Asn Lys Leu Tyr
    50                  55                  60

Leu Asp Ser Gly Thr Leu Thr Pro Leu Leu Lys Arg Leu Glu Gly Leu
65                  70                  75                  80

Asn Leu Ile Val Arg Lys Arg Ser Ser Leu Asp Glu Arg Leu Leu Ser
                85                  90                  95

Val Asn Ile Thr Glu Lys Gly Glu Glu Leu Lys Lys Asp Ala Leu Glu
            100                 105                 110

Ile Pro Ser Cys Val Leu Lys Ser Thr Asn Thr Asp Ile Glu Thr Leu
        115                 120                 125

Lys Arg Ile Lys Thr Asp Ile Asp Leu Leu Leu Lys Asn Leu Ser
    130                 135                 140

<210> SEQ ID NO 6
<211> LENGTH: 152
<212> TYPE: PRT
<213> ORGANISM: Xanthomonas axonopodis

<400> SEQUENCE: 6

Met Pro Ser Pro Gln Val Ser Cys Gln Thr Pro Thr His Asp Pro Leu
1               5                   10                  15

Leu Leu Glu Asn Gln Val Cys Phe Pro Leu Tyr Ser Ala Ser Asn Ala
            20                  25                  30

Val Ile Arg Ala Tyr Arg Pro Leu Leu Glu Gln Leu Asp Ile Thr Tyr
        35                  40                  45

Ser Gln Tyr Leu Val Leu Leu Val Leu Trp Gln Gln Asn Gly Ile Asn
    50                  55                  60

Val Lys Asp Leu Gly Ile Lys Leu His Leu Asp Ser Gly Thr Leu Thr
65                  70                  75                  80

Pro Leu Leu Lys Arg Leu Glu Ala Lys Gly Ile Val Glu Arg Arg Arg
                85                  90                  95
```

-continued

Ser Ser Ser Asp Glu Arg Val Arg Glu Leu Phe Leu Thr Pro Ala Gly
            100                 105                 110

Phe Ala Leu Gln Glu Gln Ala Arg Ser Val Pro Asn Glu Met Leu Cys
        115                 120                 125

Lys Phe Asp Leu Ser Leu Glu Glu Leu Ile Ser Leu Lys Thr Leu Cys
    130                 135                 140

Glu Lys Ile Leu His Thr Leu Asp
145                 150

<210> SEQ ID NO 7
<211> LENGTH: 153
<212> TYPE: PRT
<213> ORGANISM: Xanthomonas campestris

<400> SEQUENCE: 7

Met Asp Thr Ala Thr Pro Thr Thr Asp Arg Thr Asn Ala Leu Leu Gln
1               5                   10                  15

Leu Asp Asn Gln Leu Cys Phe Ala Leu Tyr Ser Ala Asn Leu Ala Met
            20                  25                  30

His Lys Leu Tyr Arg Gly Leu Leu Lys Thr Leu Asp Leu Thr Tyr Pro
        35                  40                  45

Gln Tyr Leu Val Met Leu Val Leu Trp Glu Asn Asp Gly Arg Ser Val
    50                  55                  60

Ser Glu Ile Gly Glu Arg Leu Tyr Leu Asp Ser Ala Thr Leu Thr Pro
65                  70                  75                  80

Leu Leu Lys Arg Leu Glu Ser Ala Gly Leu Leu Thr Arg Thr Arg Ala
                85                  90                  95

Ala His Asp Glu Arg Gln Val Ile Ile Gly Leu Ala Asp Ala Gly Arg
            100                 105                 110

Ala Leu Arg Ser Lys Ala Gly Ala Val Pro Glu Gln Val Phe Cys Ala
        115                 120                 125

Ser Ala Cys Ser Leu Glu Glu Leu Arg Gln Leu Lys Gln Glu Leu Glu
    130                 135                 140

Lys Leu Arg Thr Ser Leu Gly Ala Ala
145                 150

<210> SEQ ID NO 8
<211> LENGTH: 124
<212> TYPE: PRT
<213> ORGANISM: Staphylococcus aureus

<400> SEQUENCE: 8

Met Ala Ile Thr Lys Ile Asn Asp Cys Phe Glu Leu Leu Ser Met Val
1               5                   10                  15

Thr Tyr Ala Asp Lys Leu Lys Ser Leu Ile Lys Lys Glu Phe Ser Ile
            20                  25                  30

Ser Phe Glu Glu Phe Ala Val Leu Thr Tyr Ile Ser Glu Asn Lys Glu
        35                  40                  45

Lys Glu Tyr Tyr Leu Lys Asp Ile Ile Asn His Leu Asn Tyr Lys Gln
    50                  55                  60

Pro Gln Val Val Lys Ala Val Lys Ile Leu Ser Gln Glu Asp Tyr Phe
65                  70                  75                  80

Asp Lys Lys Arg Asn Glu His Asp Glu Arg Thr Val Leu Ile Leu Val
                85                  90                  95

Asn Ala Gln Gln Arg Lys Lys Ile Glu Ser Leu Leu Ser Arg Val Asn
            100                 105                 110

Lys Arg Ile Thr Glu Ala Asn Asn Glu Ile Glu Leu
       115                 120

<210> SEQ ID NO 9
<211> LENGTH: 10
<212> TYPE: DNA
<213> ORGANISM: Staphylococcus aureus

<400> SEQUENCE: 9
aatttgtatg                                                                10

<210> SEQ ID NO 10
<211> LENGTH: 10
<212> TYPE: DNA
<213> ORGANISM: Staphylococcus aureus

<400> SEQUENCE: 10
cagtcattgc                                                                10

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 11
cgagagctct aaatgacaca taacctttca                                          30

<210> SEQ ID NO 12
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 12
tcccccggga ttggtaatca ttaaaaagtt                                          30

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 13
ccggtcgacc ttgattagct agtaattgtt                                          30

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 14
aactgcagcg ctagttacag tcatagttt                                           29

<210> SEQ ID NO 15
<211> LENGTH: 30
<212> TYPE: DNA
<213> ORGANISM: Artificial Sequence

```
<220> FEATURE:
<223> OTHER INFORMATION: Synthetic oligonucleotide primer

<400> SEQUENCE: 15
cgagagctct aaatgacaca taacctttca                                  30

<210> SEQ ID NO 16
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 16
aactgcagcg ctagttacag tcatagttt                                   29

<210> SEQ ID NO 17
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 17
cgggatccag acattaaagt tctcctccag a                                31
```